(12) United States Patent
Biedermann et al.

(10) Patent No.: US 9,339,302 B2
(45) Date of Patent: May 17, 2016

(54) POLYAXIAL BONE ANCHORING DEVICE

(71) Applicant: BIEDERMANN TECHNOLOGIES GMBH & CO. KG, Donaueschingen (DE)

(72) Inventors: Lutz Biedermann, VS-Villingen (DE); Wilfried Matthis, Weisweil (DE); Bernd Fischer, Bräunlingen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

(21) Appl. No.: 13/906,285

(22) Filed: May 30, 2013

(65) Prior Publication Data
US 2013/0345758 A1 Dec. 26, 2013

Related U.S. Application Data

(60) Provisional application No. 61/653,747, filed on May 31, 2012.

(30) Foreign Application Priority Data

May 31, 2012 (EP) .................................... 12170300

(51) Int. Cl.
A61B 17/88 (2006.01)
A61B 17/70 (2006.01)
A61B 19/00 (2006.01)

(52) U.S. Cl.
CPC ......... *A61B 17/7032* (2013.01); *A61B 17/7037* (2013.01); *A61B 2019/307* (2013.01)

(58) Field of Classification Search
CPC ........... A61B 17/7032; A61B 17/0256; A61B 17/1671

USPC .................................. 606/264–279, 300–331
See application file for complete search history.

(56) References Cited

U.S. PATENT DOCUMENTS 6,077,262 A * 6/2000 Schlapfer et al. ............. 606/305
7,296,500 B1 * 11/2007 Martinelli ..................... 81/57.29
(Continued)

FOREIGN PATENT DOCUMENTS

EP 1323391 A2 7/2003
EP 1935358 A1 6/2008
(Continued)

OTHER PUBLICATIONS

European Search Report and Opinion issued by the EPO for EP 12170300.3 on Oct. 2, 2012 (8 pages).

*Primary Examiner* — Jerry Cumberledge
*Assistant Examiner* — Tessa Matthews
(74) *Attorney, Agent, or Firm* — Lewis Roca Rothgerber Christie LLP

(57) ABSTRACT

A polyaxial bone anchoring device is provided, comprising a bone anchoring element having a shank, a head, a receiving part for pivotably receiving the head, and a channel for receiving a rod; a pressure member configured to be arranged in the receiving part and to exert pressure onto and lock the head; a locking assembly insertable into the channel, the locking assembly comprising a first locking member having a bore; a second locking member to be provided in the bore, wherein, when the second locking member is rotated, in a first configuration, the first locking member and the second locking member are rotationally fixed relative to each other and the first locking element is advanced to contact the pressure member and in a second configuration, the second locking member is rotatable within the first locking member and the second locking member is advanced to contact the rod.

18 Claims, 6 Drawing Sheets

(56) References Cited

U.S. PATENT DOCUMENTS

| | | |
|---|---|---|
| 7,972,364 B2 | 7/2011 | Biedermann et al. |
| 8,088,152 B2 | 1/2012 | Schumacher |
| 2002/0143341 A1 | 10/2002 | Biedermann et al. |
| 2003/0100896 A1 | 5/2003 | Biedermann et al. |
| 2003/0125741 A1 | 7/2003 | Biedermann et al. |
| 2004/0236330 A1* | 11/2004 | Purcell et al. ............... 606/61 |
| 2005/0131410 A1 | 6/2005 | Lin |
| 2005/0187548 A1 | 8/2005 | Butler et al. |
| 2005/0216003 A1* | 9/2005 | Biedermann et al. ........... 606/61 |
| 2006/0149235 A1* | 7/2006 | Jackson ........................ 606/61 |
| 2006/0276789 A1* | 12/2006 | Jackson ........................ 606/61 |
| 2007/0118123 A1* | 5/2007 | Strausbaugh et al. ......... 606/61 |
| 2008/0039848 A1* | 2/2008 | Jackson ........................ 606/73 |
| 2009/0012567 A1* | 1/2009 | Biedermann et al. ......... 606/264 |
| 2009/0248030 A1* | 10/2009 | Butler et al. ................ 606/104 |
| 2010/0160981 A1 | 6/2010 | Butler et al. |
| 2011/0218579 A1* | 9/2011 | Jackson ............. A61B 17/7032 606/305 |
| 2012/0150232 A1* | 6/2012 | Van Nortwick et al. ...... 606/264 |
| 2013/0103093 A1* | 4/2013 | Biedermann et al. ......... 606/272 |
| 2014/0081334 A1* | 3/2014 | Jackson ............. A61B 17/7035 606/278 |
| 2014/0142633 A1* | 5/2014 | Jackson ............. A61B 17/7032 606/273 |

FOREIGN PATENT DOCUMENTS

| | | |
|---|---|---|
| EP | 2070485 A1 | 6/2009 |
| EP | 2286748 A1 | 2/2011 |
| WO | WO 02/076314 A1 | 10/2002 |
| WO | WO 2006/047555 A2 | 5/2006 |
| WO | WO 2007/075454 A1 | 7/2007 |

\* cited by examiner

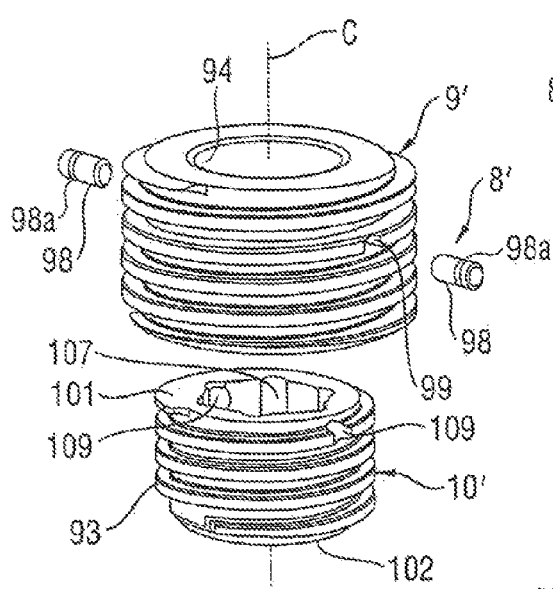
Fig. 18
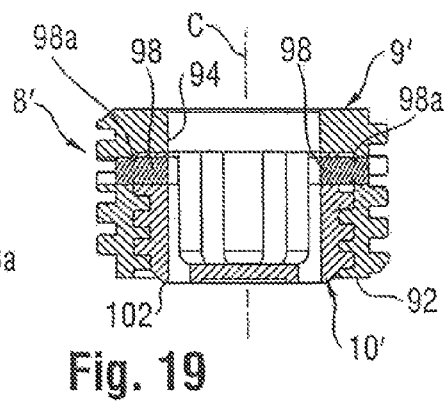
Fig. 19
Fig. 20
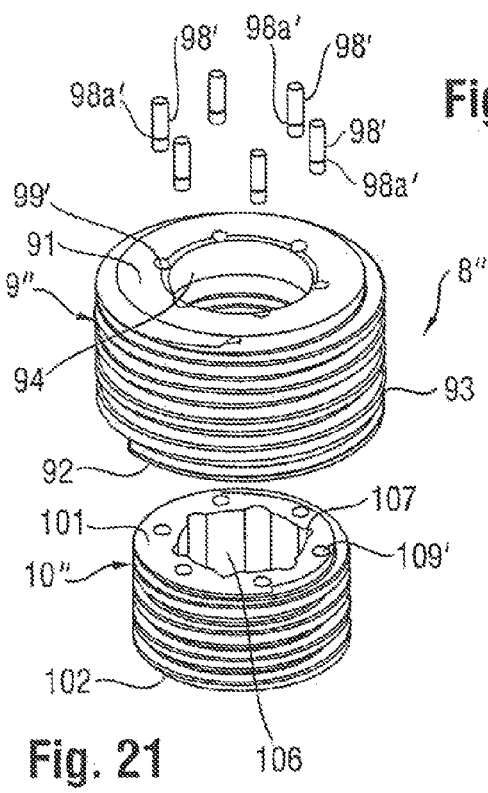
Fig. 21
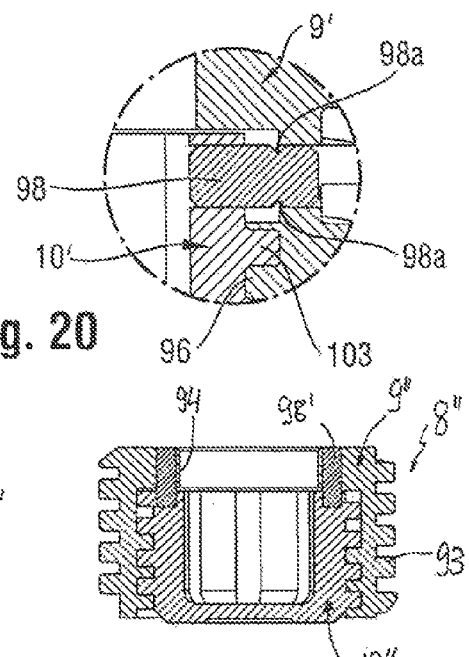
Fig. 22
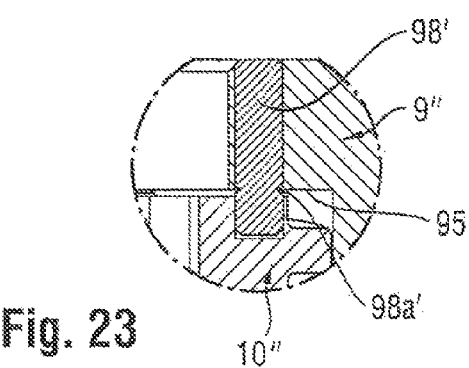
Fig. 23

POLYAXIAL BONE ANCHORING DEVICE

CROSS-REFERENCE TO RELATED APPLICATIONS

The present disclosure claims the benefit of U.S. Provisional Patent Application Ser. No. 61/653,747, filed May 31, 2012, the contents of which are hereby incorporated by reference in their entirety, and claims priority from European Patent Application EP 12 170 300.3, filed May 31, 2012, the contents of which are hereby incorporated by reference in their entirety.

BACKGROUND

1. Field of the Invention

The invention relates to a polyaxial bone anchoring device, in particular for use in spinal or trauma surgery. The polyaxial bone anchoring device comprises a bone anchoring element with a shank to be anchored in the bone and a head. The head is pivotably held in a receiving part and can be fixed at an angle by applying pressure onto it via a pressure element. The polyaxial bone anchoring device further includes a locking assembly comprising a first locking member being configured to exert pressure onto the pressure member and a second locking member provided in a bore of the first locking member, the second locking member being configured to exert pressure onto the rod. In a first configuration, the first and the second locking members are rotationally fixed relative to each other such that by rotating the second locking member in a first direction, the first locking member is advanced to contact the pressure member. In a second configuration, the second locking member is rotatable within the first locking member such that by rotating the second locking member in the first direction, the second locking member is advanced to contact the rod. With the locking assembly, the head and the rod can be fixed in a sequential manner using a tool with a single drive portion that engages the second locking member.

2. Description of the Related Art

US 2003/0100896 A1 describes a bone anchoring device with a shank and a receiving part connected to it for connecting to a rod. The receiving part has a recess having a U-shaped cross-section for receiving the rod with two open legs and an internal thread on the open legs. A locking assembly is provided comprising a nut member with an external thread that cooperates with the internal thread of the legs and a set screw. The nut member has on one end slits for engagement with the screw tool. The shank has a spherically-shaped head that is pivotably held in the receiving part. A pressure element is provided that exerts pressure onto the head when the nut member is tightened. By tightening the set screw the rod is fixed in a receiving part. Hence, the rod and the head can be locked independently from each other.

U.S. Pat. No. 7,972,364 describes a locking assembly for securing a rod in a rod receiving part of a bone anchoring device that includes a first locking element and a second locking element. With the first locking element and the second locking element the head of the bone anchoring element and the rod can be locked independently using a tool with two drive portions.

U.S. Pat. No. 8,088,152 B2 describes an orthopedic retaining system comprising at least one bone screw which has a head part and a threaded shaft pivotably mounted thereon. A clamping element is mounted in the head part, which can be pressed against the threaded shaft from its upper side and, as a result, secure the threaded shaft relative to the head part. A retaining bar is arranged in a receptacle of the head part. Further, a clamping device is provided on the upper side of the head part, by means of which the clamping element and the retaining bar are pressed into the head part such that the threaded shaft and the retaining bar are secured in positions relative to the head part. The clamping device comprises an elastically deformable pressure element which is displaced into a clamping position during actuation of the clamping device. With such a configuration, upon actuation of the clamping device, the pressure element abuts first on the clamping element and thereby secures the pivotable threaded shaft in position on the head part while the retaining bar remains freely displaceable. Only upon further actuation of the clamping device the pressure element is elastically deformed thereby abutting on the retaining bar and securing the retaining bar in position.

SUMMARY

It is an object of the invention to provide an improved polyaxial bone anchoring device that provides for simplified handling and reliable clamping of the head and the rod.

In one embodiment, the polyaxial bone anchoring device allows locking the head of the bone anchoring element in the receiving part and the rod in a sequential manner using only a single tool with a single drive portion. By this sequential locking mechanism it is possible to first lock or at least preliminarily clamp the head and thereafter finally lock the rod and the head. More specifically, a full locking of the head and the rod can be carried out and thereafter the fixation of the rod can be loosened to perform adjustments of the rod. Because only a single tool with a single drive portion is needed for performing these steps, the use of the locking assembly is facilitated.

In an embodiment of the invention, the locking assembly can be pre-assembled in a first configuration wherein the second locking member is rotationally fixed with respect to the first locking member such that a predetermined torque is necessary to release the second locking member with respect to the first locking member. When the locking assembly is advanced towards the pressure member in this configuration, the abutment of the first locking member on the pressure member overcomes the predetermined torque by further rotation of the second locking member. Hence, because the second locking member is released from its provisional fixation, an over-tightening of the first locking member in the receiving part can not occur. Also, the second locking member is protected against falling out in the first configuration which increases the safety of the device during handling.

The polyaxial bone anchoring device can be designed as a low profile polyaxial bone anchoring device with reduced height. This is possible, because the first locking element can be designed free from any drive portions for engagement with a tool.

In one embodiment, when the locking assembly assumes a second configuration in which the second locking member is rotatable with respect to the first locking member in the first direction, a feedback is given to the person holding the tool. This further improves the handling of the device.

The polyaxial bone anchoring device comprises only few parts. The locking assembly can be used with existing polyaxial bone anchoring devices that allow a separate head and rod fixation.

BRIEF DESCRIPTION OF THE DRAWINGS

Further features and advantages will become apparent from and will be best understood by reference to the following detailed description reviewed in conjunction with the accompanying drawings. In the drawings:

FIG. 18 shows a perspective exploded view of a locking assembly of a polyaxial bone anchoring device according to a second embodiment.

FIG. 19 shows a cross-sectional view of the locking assembly according to the second embodiment.

FIG. 20 shows an enlarged view of a portion of FIG. 19.

FIG. 21 shows a perspective exploded view of a locking assembly according to a modified second embodiment of the polyaxial bone anchoring device.

FIG. 22 shows a cross-sectional view of the locking assembly according to the modified second embodiment.

FIG. 23 shows an enlarged portion of FIG. 22.

DETAILED DESCRIPTION

Figure 1:
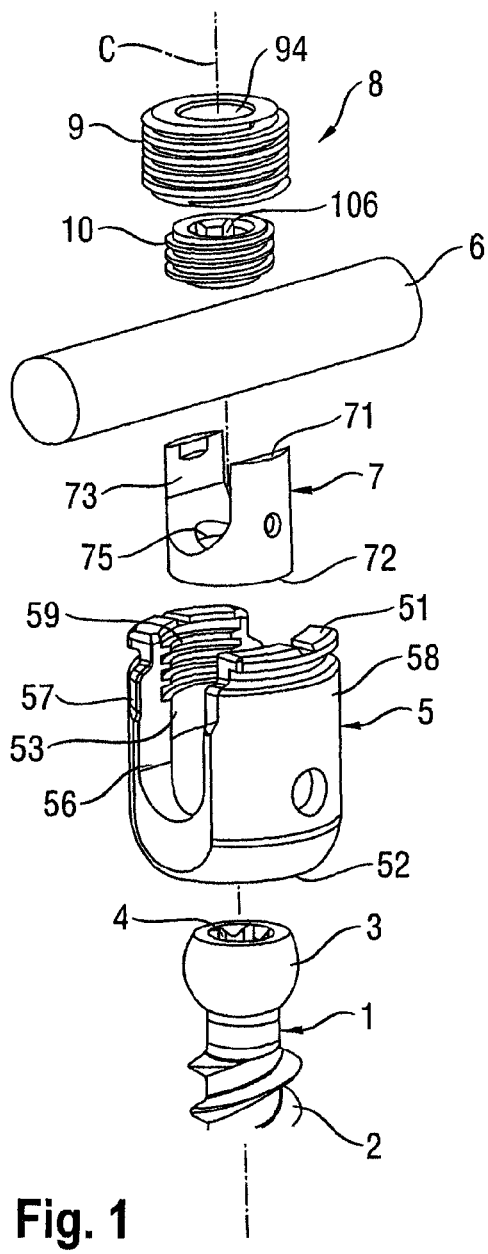
FIG. 1 shows a perspective exploded view of a bone anchoring device according to a first embodiment.
Figure 2:
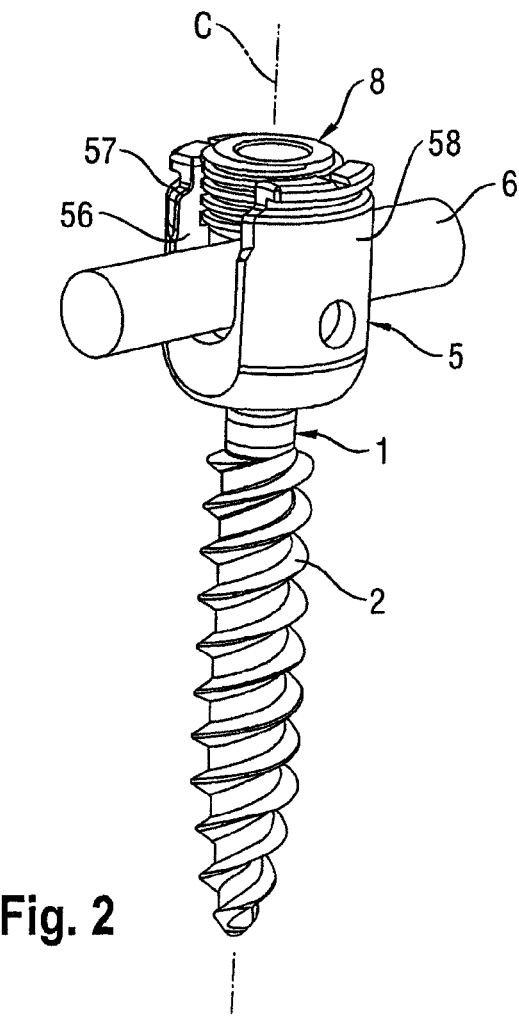
FIG. 2 shows a perspective view of the polyaxial bone anchoring device according to the first embodiment in an assembled state.

The polyaxial bone anchoring device according to a first embodiment is shown in FIGS. 1 and 2. It comprises an anchoring element 1 having a shank 2 with a threaded portion and a head 3. The head 3 has a spherically-shaped outer surface portion and, on its side opposite to the shank 2, a recess 4 for engagement with a tool. A receiving part 5 is provided for coupling the bone anchoring element 1 to a rod 6. In the receiving part 5, a pressure member 7 is arranged to exert pressure onto the head 3 of the bone anchoring element 1.

The bone anchoring device further comprises a locking assembly 8 having a first locking member 9 and a second locking member 10 coupled to the first locking member 9.

Figure 12:
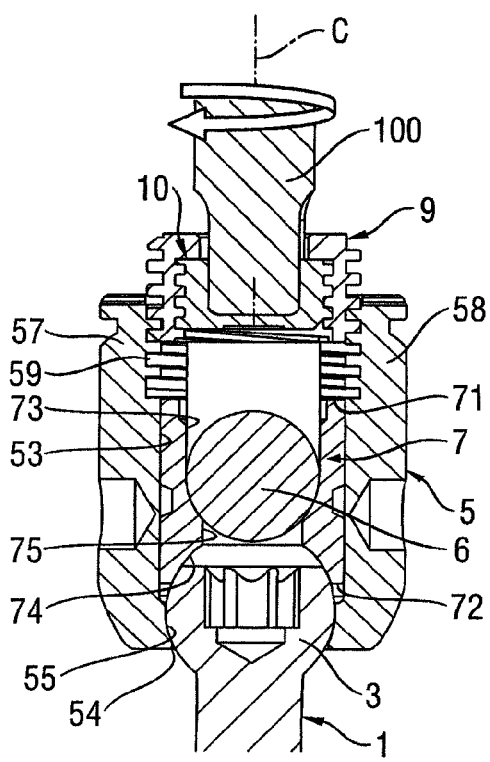
FIGS. 12 to 15 show the steps of mounting of the locking assembly in the polyaxial bone anchoring device and the use of the locking assembly according to a first embodiment.

Referring to FIGS. 1 and 2 as well as FIG. 12, the receiving part 5 has a top end 51 and a bottom end 52 and is of substantially cylindrical construction with a longitudinal axis C extending through the top end 51 and the bottom end 52. Coaxially with the longitudinal axis C, a bore 53 is provided extending from the top end 51 to a predetermined distance from the bottom end 52. At the bottom end 52, an opening 54 is provided, the diameter of which is smaller than the diameter of the bore 53. The coaxial bore narrows towards the opening 54, for example, with a spherically-shaped section 55 that provides a seat for the head 3. However, the section 55 can have any other shape such as, for example, a conical shape, that ensures that the head 3 is being pivotably held in the receiving part 5 similar to a ball and socket joint.

The receiving part 5 further comprises a U-shaped recess 56 starting at the top end 51 and extending in the direction of the bottom end 52. By means of the U-shaped recess 56, two free legs 57, 58 are formed that are open towards the top end 51 and define a channel for receiving the rod 6. Adjacent to the top end 51, a portion with an internal thread 59 is provided at the inner surface of the legs 57, 58. In the embodiment shown, the internal thread 59 is a flat thread having substantially horizontal upper and lower thread flanks. Any other thread form can be used for the internal thread 59, however, a thread form that reduces or eliminates splaying of the legs is preferable.

The pressure member 7 is of substantially cylindrical construction with an outer diameter sized so as to allow the pressure member to be introduced into the bore 53 of the receiving part 5 and to be moved therein in the axial direction. The pressure member 7 has a top end 71 and an opposite bottom end 72 and a longitudinal axis C extending through the two ends being in a mounted state the same as the longitudinal axis C of the receiving part 5. The pressure element is arranged in the receiving part 5 such that its top end 71 is oriented towards the top end 51 of the receiving part and the bottom end 72 is oriented towards the bottom end 52 of the receiving part. At its top end 71, the pressure element 7 comprises a substantially U-shaped recess 73 that is configured to receive the rod 6. When the rod 6 is positioned on the bottom of the recess 73, the top end 71 of the pressure member 7 is located at a height above the surface of the rod 6. On its lower side, the pressure member 7 comprises a spherically-shaped recess 74 that cooperates with a spherical outer surface portion of the head 3. Furthermore, a coaxial through-hole 75 is provided in the pressure member 7 that allows access to the recess 4 of the head 3 when the bone anchoring element 1 and the pressure member 7 are mounted in the receiving part 5.

Figure 3:
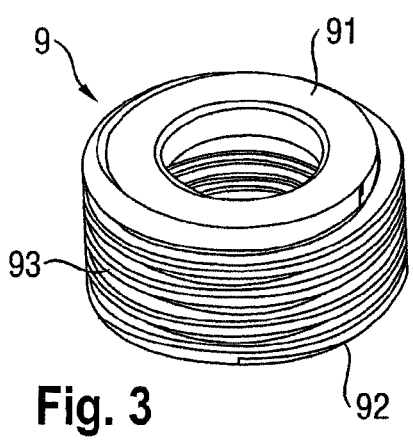
FIG. 3 shows a perspective view from the top of a first locking member of a locking assembly of the polyaxial bone anchoring device according to the first embodiment.
Figure 4:
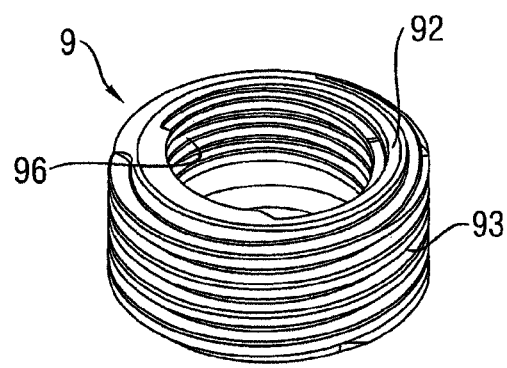
FIG. 4 shows a perspective view from the bottom of the first locking member of the locking assembly shown in FIG. 3.
Figure 5:
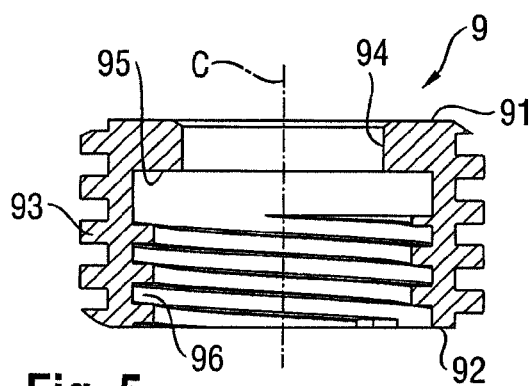
FIG. 5 shows a cross-sectional view of the first locking member of FIG. 3.
Figure 6:
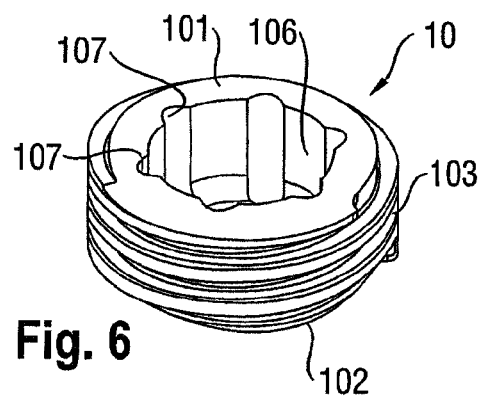
FIG. 6 shows a perspective view from the top of the second locking member of the locking assembly according to the first embodiment.

As can be seen in particular in FIGS. 3 to 5, the first locking element 9 of the locking assembly 8 is a screw member having a top end 91 and a bottom end 92. The first locking member 9 forms an outer locking member in the assembly 8. Between the top end 91 and the bottom end 92 an outer surface portion with an external thread 93 is provided that cooperates with the internal thread 59 of the receiving part 5. A coaxial through-hole 94 extends from the top end 91 to the bottom end 92. Starting at a distance from the top end 91 down until the bottom end 92 the through-hole 94 has an enlarged diameter such that, as can be seen from the bottom end 92 looking in the direction to the top end 91, an annular abutment 95 is formed near the top end 91. Further, the first locking member 9 has an inner surface portion with an internal thread 96 that extends preferably from the bottom end 92 to a distance from the abutment 95. The internal thread 96 may be a flat thread. A flat thread is capable of transferring high loads. The thread pitch of the internal thread 96 and the external thread 93 are preferably the same. However, they can also be different.

Figure 7:
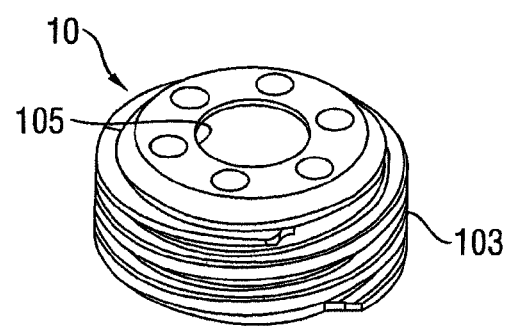
FIG. 7 shows a perspective view from the bottom of the second locking member of the locking assembly shown in FIG. 6.
Figure 8:
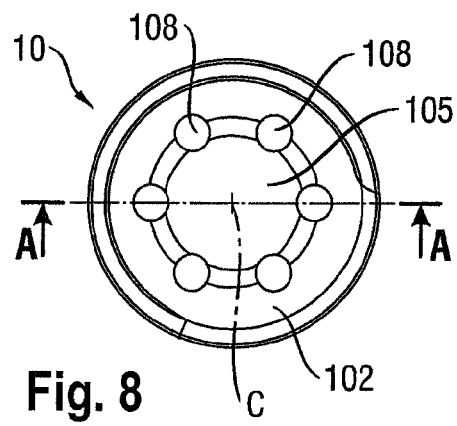
FIG. 8 shows a bottom view of the second locking member of FIG. 6.
Figure 9:
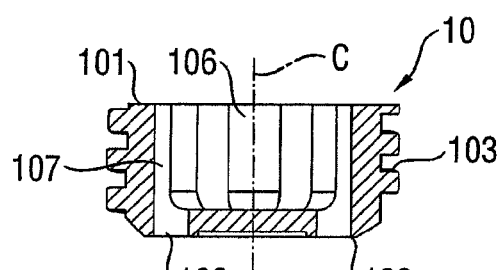
FIG. 9 shows a cross-sectional view along line A-A in FIG. 8.

The second locking member 10 forms an inner locking member of the assembly 8. Referring now to FIGS. 7 to 9, the second locking member 10 comprises a top end 101 and a bottom end 102 and an external thread 103 that is configured to cooperate with the internal thread 96 of the first locking member 9. A coaxial through-hole 105 is provided that extends from the bottom end 102 to the top end 101. Furthermore, adjacent to the top end 101 a cylindrical recess 106 is provided that has an inner diameter that is greater than the diameter of the through-hole 105. In addition, adjacent to the top end 101, there is an engagement structure in the form of a plurality of coaxial longitudinal grooves 107 that allow for engagement with an insertion and drive tool. The longitudinal grooves 107 open into the face of the second end 102 thereby forming circular holes 108. The holes 108 can serve as an engagement structure for a tool to mount the second locking member 10 into the first locking member 9 from the second end 92 of the first locking member 9. The axial height of the second locking member 10 is such that the second locking member 10 can be completely accommodated within the first locking member 9.

Figure 10:
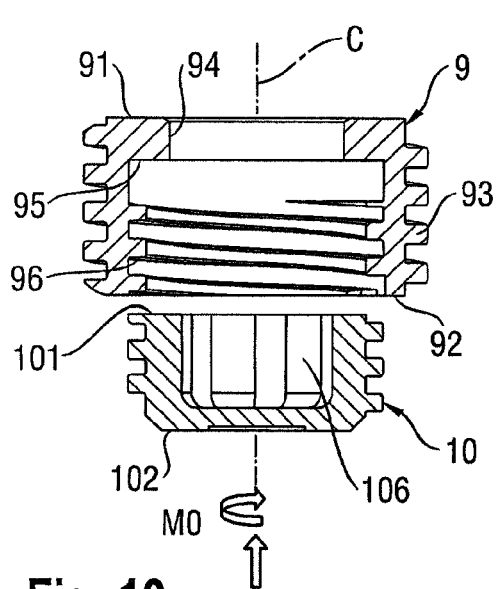
FIGS. 10 and 11 show steps of pre-assembling of the locking assembly of the polyaxial bone anchoring device according to the first embodiment.
Figure 11:
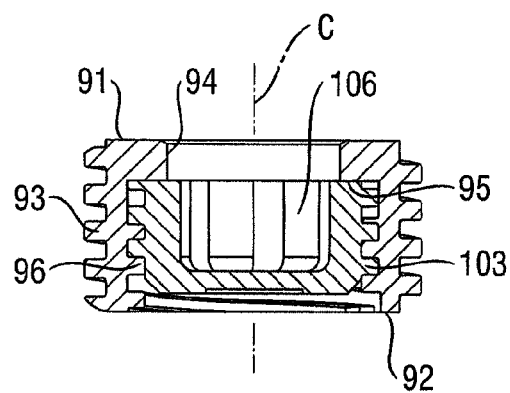

The steps of assembling the first and the second locking members, 9, 10 of the locking assembly 8 will be explained with reference to FIGS. 10 and 11. In a first step, the second locking member 10 is introduced into the first locking member 9 with its top end 101 facing the second end 92 of the first locking member 9. The second locking member 10 is then screwed into the threaded bore 94, 96 of the first locking member 9 until its top end 101 abuts against the abutment 95, as shown in FIG. 11. Then, the second locking member 10 is tightened with a predefined tightening torque M0 against the abutment 95. By means of this, the first locking member 9 and the second locking member 10 are rotationally fixed with respect to each other in a provisional manner. To release the second locking member 10 from the provisional fixation a torque M2 has to be applied in the opposite direction that is greater than a predetermined release torque M1. The release torque M1 may be the same or may be smaller than the tightening torque M0 because of losses due to friction and other effects. The provisional fixation prevents the second locking member 10 from being advanced towards the second end 92 of the first locking member 9 when it is engaged with a tool in the engagement portion 106, 107 and when a torque is applied that is smaller than the release torque M1. In addition, the abutment 95 prevents the second locking member 10 from passing through the top end 91 of the first locking member.

The parts of the bone anchoring device are made of a biocompatible material, for example, of a biocompatible metal or metal alloy, such as titanium, stainless steel, nickel titanium alloys such as Nitinol or made of a biocompatible plastic material, such as PEEK (polyetheretherketone). The parts can be made all of the same or of different materials.

In use, the receiving part 5 and the anchoring element 1 as well as the pressure member 7 are usually pre-assembled such that the head 3 is pivotably held in the seat 55 of the receiving part 5 and the pressure member 7 is placed onto the head 3. Usually at least two polyaxial bone anchoring devices are used and connected via a rod 6. After insertion of the bone anchoring element 1 into the bone the receiving parts are aligned and the rod 6 is inserted.

In a first step, shown in FIG. 12, the pre-assembled locking assembly 8 is engaged with a tool 100 that is inserted into the engagement structure 106, 107 provided in the second locking member 10. Thereafter it is inserted between the legs 57, 58 of the receiving part 5 and advanced in a first direction towards the rod 6 and the pressure member 7. The torque applied to the second locking member 10 with the tool 100 for screwing-in the first locking member 9 between the legs 57, 58 is smaller than the release torque M1. Therefore, the first locking member 9 and the second locking member 10 remain in the first configuration where they are rotationally fixed with respect to each other in a provisional manner.

Figure 13:
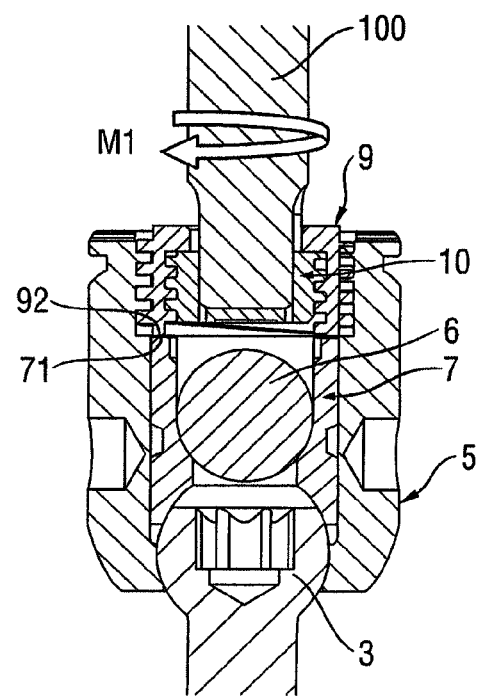
Figure 14:
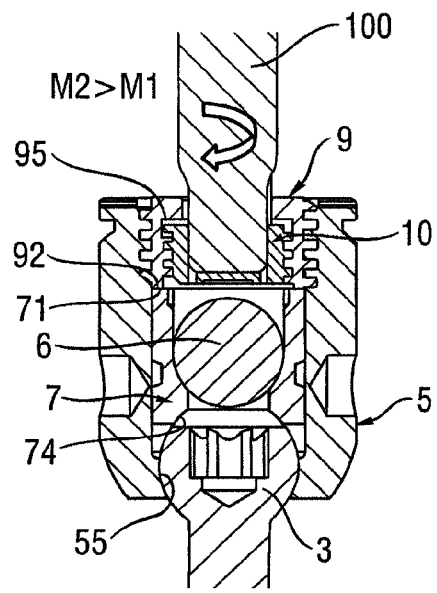

As shown in FIG. 13, when the first locking member 9 touches with a surface portion of its bottom end 92 a surface portion of the pressure member 7 at the top end 71, the torque applied to the second locking member 10 increases until an applied torque M2 is reached that is greater than the release torque M1 and the second locking member 10 is released from the abutment 95 and advanced through the first locking member 9, as shown in FIG. 14. Simultaneously, the pressure exerted by the first locking member 9 onto the pressure member 7 is transferred to the head 3 of the bone anchoring element 1. By means of this, the pressure member 7 exerts pressure onto the head 3 that clamps the head 3 by friction. In this configuration, the bone anchoring element 1 can be maintained in a certain angular position with respect to the receiving part 5, whereas the rod 6 is still displaceable in the recess 73. Release of the second locking member gives a feedback to the surgeon that allows for precise adjustments.

Figure 15:
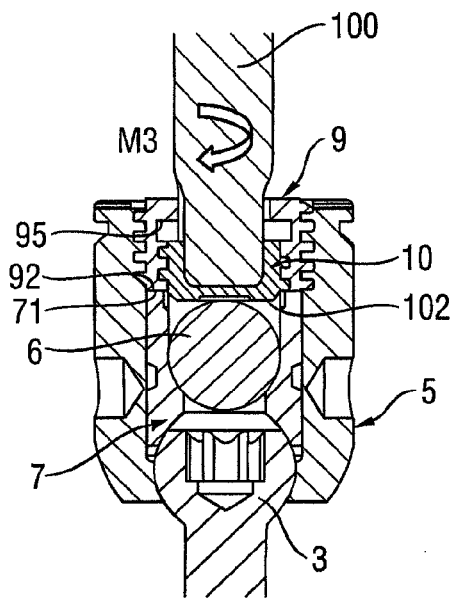

Finally, as shown in FIG. 15, the second locking element 10 is further advanced until its bottom end 102 contacts the rod 6. The rod 6 is then finally fixed by applying a torque M3 that also fully locks the assembly.

Figure 16:
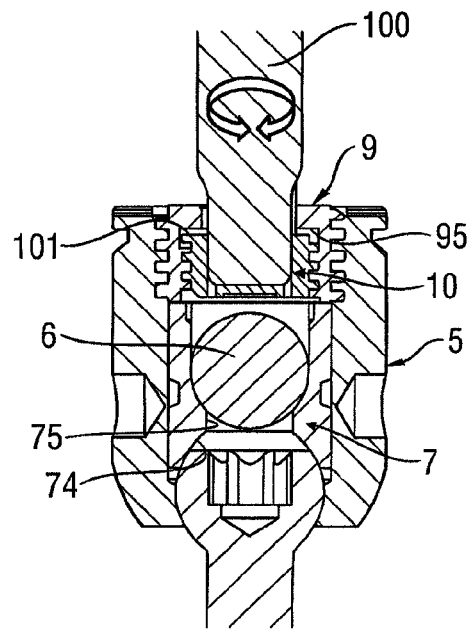
FIGS. 16 and 17 show steps of correction of the rod position and of removal of the locking assembly from the polyaxial bone anchoring device according to a first embodiment.

FIG. 16 shows the step of correcting the position of the rod 6. To achieve this, the tool 100 engages the engagement portion 106, 107 of second locking member 10 and the second locking member 10 is rotated in the second direction towards the abutment 95 so that the rod 6 becomes displaceable. Then a correction of the position of the rod 6 with respect to the receiving part 5 can be made. Thereafter, the second locking member is rotated in the first direction until it locks the rod 6 again.

Figure 17:
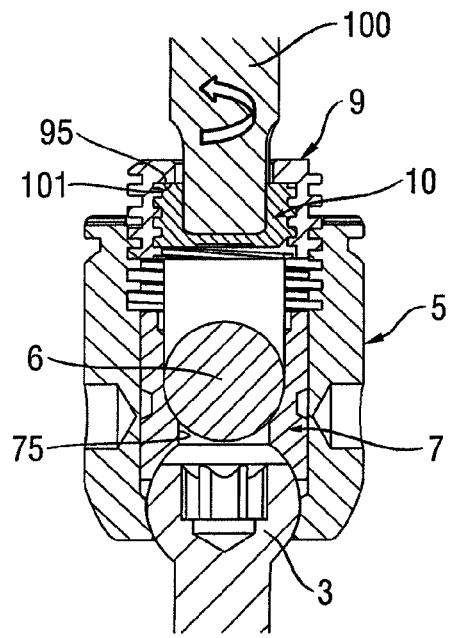

For the purpose of a complete revision of the polyaxial anchoring device the locking assembly 8 can be removed as a whole as shown in FIG. 17. The second locking member 10 is engaged by the tool 100 and screwed into the bore of the first locking member 9 until it abuts against the abutment 95. The abutment 95 prevents further movement of the second locking member and the locking assembly 8 can be screwed out, thereby releasing the locking of the head 3.

A second embodiment of the polyaxial bone anchoring will be described with reference to FIGS. 18 to 20. The second embodiment differs from the first embodiment in the design of the locking assembly 8'. The locking assembly 8' comprises a device for providing a provisional rotational fixation between the first locking member 9' and the second locking member 10'. The device for provisional rotational fixation is in this embodiment at least one shear pin 98, preferably two shear pins 98 that are arranged opposite to each other seen in a circumferential direction around the central axis C. The shear pins 98 extend into corresponding bores 99, 109 of the first and the second locking members 9', 10' extending in radial direction with respect to the central axis C. The shear pins 98 are arranged in a substantially press-fit manner in the bores, respectively, and have a length such that they do not hinder the engagement of the recess 106, 107 with the tool 100 and do not project into the external thread 93 of the first locking member 9'. The bores 99, 109 are arranged at a small distance from the abutment 95.

The shear pins 98 have a predetermined breaking area 98a that is, when the pins 98 are inserted, arranged preferably at a distance from the central axis that corresponds substantially to the distance that the root of the internal thread 96 of the first locking member 9' is from the central axis, as shown in particular in FIG. 20. The predetermined breaking area 98a may be realized as a portion of the pin 98 that has a reduced diameter or a neck.

In use, when the first locking member 9' abuts against the pressure member 7 and the torque applied to the second locking member 10' is increased, a force is exerted onto the shear pins 98 that breaks the shear pins 98 into two portions at the predetermined breaking area. The two portions of the pins remain within the bores. Because the locking assembly is inserted into the receiving part, the portions of the shear pins 98 are also secured against loss. It has to be understood that depending on the desired release torque M1 the number of pins 98 as well as the thickness and other features of the pins 98 may vary.

In a modification of the second embodiment, the locking assembly 8" that is shown in FIGS. 21 to 23 comprises a plurality of shear pins 98' that are oriented coaxially to the central axis C. The shear pins 98' extend from the top end 91 of the first locking member 9" into the top end 101 of the second locking member 10". A predetermined breaking area 98a' is provided between the top end 101 of the second locking member 10" and the abutment 95. As in the previous embodiment, at least one pin may be sufficient.

Figure 24:
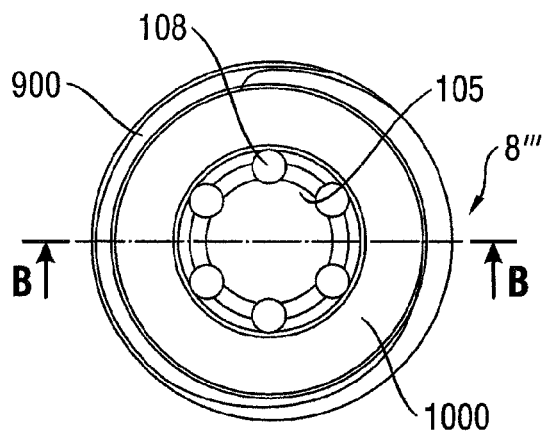
FIG. 24 shows a bottom view of a locking assembly according to a third embodiment of the polyaxial bone anchoring device.
Figure 25:
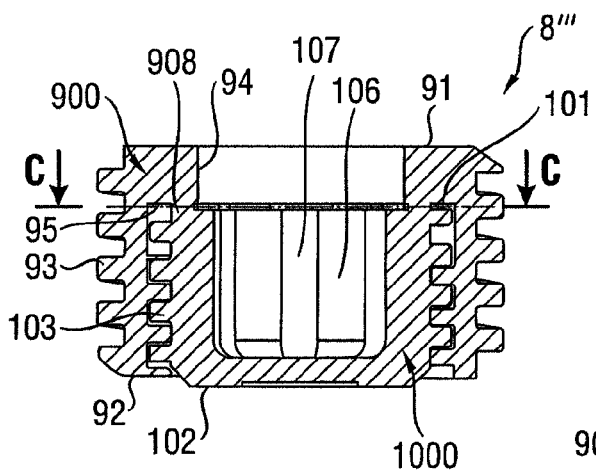
FIG. 25 shows a cross-sectional view of the locking assembly according to a third embodiment, the cross-section taken in a plane containing the bore axis C.
Figure 26:
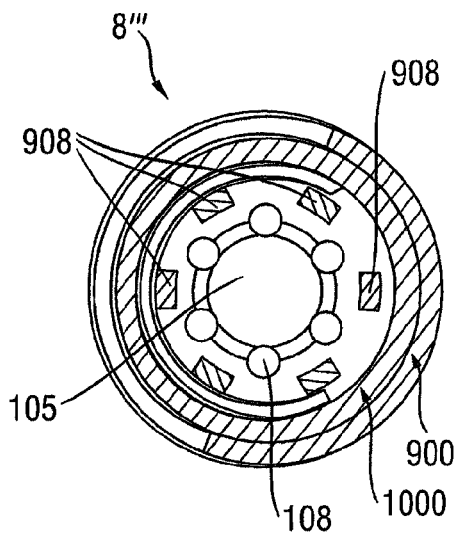
FIG. 26 shows a cross-sectional view of the locking assembly along line C-C in FIG. 25.

FIGS. 24 to 26 show a third embodiment of the locking assembly 8''' of the polyaxial bone anchoring device. The locking assembly 8''' of the third embodiment comprises a first locking member 900 and a second locking member 1000 that are in a first configuration made as a monolithic piece. They are shaped identically as in the first embodiment and the description of the same parts will not be repeated. To achieve the provisional rotational fixation the first locking member 900 and the second locking member 1000 are connected at the top end 101 of the second locking member 1000 and the abutment 95 of the first locking member 900 monolithically via predetermined breaking areas 908. The predetermined breaking areas 908 are arranged at circumferentially distinct areas around the central axis C and have such a size that they break when a torque is applied to the second locking member 1000 that is greater than the release torque M1. The predetermined breaking areas 908 may have any suitable shape. They may also be located at another position on the locking members 900, 1000.

In the second and the third embodiment, the second locking member 10', 10", 1000 may project out of the first locking member 9', 9", 900 in the first configuration. Hence, the U-shaped recess of the pressure member 7 may be made deeper, such that the first locking member 9', 9", 900 can press onto the top end of the pressure member 7 without the second locking member 10', 10", 1000 contacting the rod 6.

In use, when the bottom end 92 of the first locking member 900 abuts against the top end 71 of the pressure member 7 and when a torque M2 greater than the release torque M1 is applied to the second locking member 1000 the connection is broken and the second locking member 1000 can be screwed in towards the rod 6.

The locking assembly 8''' of the third embodiment can be manufactured, for example, by an additive layer manufacturing method wherein the locking assembly 8''' is made layer by layer from a material that is solidified at the cross-section of the assembly in each layer. Such an additive manufacturing method can be, for example, laser or electron gun sintering or melting.

Modifications of the above described embodiments are conceivable. The device for provisionally fixing the second locking member to the first locking member can have any construction that allows to provisionally hold the pieces together, for example, a welding point that is broken or a spring that is pressed away when the predetermined torque is exceeded.

For the polyaxial bone anchoring device any known polyaxial bone anchoring device can be used that comprises a bone anchoring element pivotably received in a receiving part and a rod. As bone anchoring element, any known bone anchors, such as screws, nails, with or without cannulation can be used.

Instead of the threaded connection between the receiving part and the first locking member on the one hand and between the first locking member and the second locking member on the other hand, any other engagement structure can be used that allows a defined advancement in the axial direction.

The invention claimed is:

1. A polyaxial bone anchoring device comprising:
   a bone anchoring element having a shank to be anchored to a bone and a head;
   a receiving part configured to be coupled to the shank and to pivotably receive the head, and having a channel for receiving a rod and a central axis;
   a pressure member configured to be received in the receiving part and to exert pressure onto the head to lock the head in the receiving part;
   a locking assembly that is insertable into the channel, the locking assembly comprising
   a first locking member having a first end, a second end configured to face the pressure member, and a bore passing through the first locking member from the first end to the second end, the bore having a bore axis;
   a second locking member configured to be provided in the bore of the first locking member, the second locking member having a first end, a second end and an engagement portion for a tool, wherein the first end of the second locking member is insertable into the second end of the first locking member such that the first end of the second locking member is directed towards the first end of the first locking member when the locking members are assembled; and
   wherein
   in a first configuration in which the locking members are assembled in the channel, the first locking member and the second locking member are rotationally fixed relative to each other such that by application of a first torque to the second locking member via the engagement portion in a first direction, the first locking member is rotatable together with the second locking member in the first direction and configured to be advanced in an axial direction to contact the pressure member with at least a surface portion of its second end and
   in a second configuration in which the locking members are assembled in the channel, the second locking member is rotatable within the first locking member such that by rotating the second locking member via the engagement portion in the first direction, the second locking member is configured to be advanced in the axial direction to contact the rod with at least a surface portion of its second end,
   wherein in the first configuration, the first end of the second locking member abuts against an abutment of the first locking member.

2. The polyaxial bone anchoring device of claim 1, wherein the second locking member is rotatable relative to the first locking member in the first direction by application of a second torque to the second locking member that is greater than a predetermined torque.

3. The polyaxial bone anchoring device of claim 2, wherein the second torque that is greater than the predetermined torque is applied to the second locking member when the first locking member abuts against the pressure member.

4. The polyaxial bone anchoring device of claim 2, wherein in the first configuration, the second locking member is tightened in a second direction to abut against the abutment of the first locking member with the predetermined torque.

5. The polyaxial bone anchoring device of claim 1, wherein the locking assembly comprises a single drive portion for a tool that is provided by the engagement portion on the second locking member.

6. The polyaxial bone anchoring device of claim 1, wherein the abutment provides a stop that prevents movement of the second locking member out of the first end of the first locking member.

7. The polyaxial bone anchoring device of claim 1, wherein the pressure member is a monolithic piece with a channel to receive the rod and wherein sidewalls of the channel of the pressure member extend above the surface of the rod when the rod is seated in the channel of the pressure member.

8. The polyaxial bone anchoring device of claim 1, wherein the bore in the first locking member is at least partially threaded and wherein the second locking member comprises an outer threaded surface portion that cooperates with the threaded bore.

9. The polyaxial bone anchoring device of claim 1, wherein the receiving part comprises a top end and a bottom end, a bore extending from the top end to the bottom end and wherein the channel for the rod is formed by a recess adjacent to the top end with a substantially U-shaped cross-section.

10. The polyaxial bone anchoring device of claim 9, wherein by the recess two open legs are formed and wherein an internal thread is provided on the legs that cooperates with an external thread on the first locking member.

11. The polyaxial bone anchoring device of claim 1, wherein, when the locking assembly is moved from the first configuration to a position wherein the first locking member abuts against the pressure member, the head is clamped without clamping the rod.

12. The polyaxial bone anchoring device of claim 1, wherein, when the second locking member is moved from the second configuration to a position whereby the second locking member abuts the rod, the rod is fixed.

13. The polyaxial bone anchoring device of claim 1, wherein the engagement portion of the second locking member is at the first end of the second locking member, and the second locking member further comprises another engagement portion for a tool at the second end of the second locking member.

14. The polyaxial bone anchoring device of claim 1, wherein the first locking member does not have any drive portion for engagement with a tool.

15. A polyaxial bone anchoring device comprising:
a bone anchoring element having a shank to be anchored to a bone and a head;
a receiving part configured to be coupled to the shank and to pivotably receive the head; and having a channel for receiving a rod and a central axis;
a pressure member configured to be received in the receiving part and to exert pressure onto the head to lock the head in the receiving part;
a locking assembly that is insertable into the channel, the locking assembly comprising
a first locking member having a first end a second end configured to face the pressure member, and a bore passing in the first locking member from the first end toward the second end, the bore having a bore axis;
a second locking member configured to be provided in the bore of the first locking member, the second locking member having a first end, a second end and an engagement portion for a tool, wherein the first end of the second locking member is directed towards the first end of the first locking member when the locking members are assembled; and
wherein
in a first configuration in which the locking members are assembled in the channel, the first locking member and the second locking member are rotationally fixed relative to each other such that by application of a first torque to the second locking member via the engagement portion in a first direction, the first locking member is rotatable together with the second locking member in the first direction and configured to be advanced in an axial direction to contact the pressure member with at least a surface portion of its second end and
in a second configuration in which the locking members are assembled in the channel, the second locking member is rotatable within the first locking member such that by rotating the second locking member via the engagement portion in the first direction, the second locking member is configured to be advanced in the axial direction to contact the rod with at least a surface portion of its second end, and
wherein in the first configuration the first locking member and the second locking member are rotationally fixed with respect to each other by at least one predetermined breaking area provided on at least one shear pin.

16. The polyaxial bone anchoring device of claim 15, wherein the at least one shear pin extends from the first locking member into the second locking member and wherein the at least one predetermined breaking area is located at the border between the first locking member and the second locking member.

17. A polyaxial bone anchoring device comprising:
a bone anchoring element having a shank to be anchored to a bone and a head;
a receiving part configured to be coupled to the shank and to pivotably receive the head, and having a channel for receiving a rod and a central axis;
a pressure member configured to be received in the receiving part and to exert pressure onto the head to lock the head in the receiving part;
a locking assembly that is insertable into the channel, the locking assembly comprising
a first locking member having a first end, a second end configured to face the pressure member, and a bore passing in the first locking member from the first end toward the second end, the bore having a bore axis;
a second locking member configured to be provided in the bore of the first locking member, the second locking member having a first end, a second end and an engagement portion for a tool, wherein the first end of the second locking member is directed towards the first end of the first locking member when the locking members are assembled; and
wherein
in a first configuration in which the locking members are assembled in the channel, the first locking member and the second locking member are rotationally fixed relative to each other such that by application of a first torque to the second locking member via the engagement portion in a first direction, the first locking member is rotatable together with the second locking member in the first direction and configured to be advanced in an axial direction to contact the pressure member with at least a surface portion of its second end and in a second configuration in which the locking members are assembled in the channel, the second locking member is rotatable within the first locking member such that by rotating the second locking member via the engagement portion in the first direction, the second locking member is configured to be advanced in the axial direction to contact the rod with at least a surface portion of its second end, and wherein in the first configuration, the locking assembly comprising the first locking member and the second locking member is formed as a monolithic piece with at least one predetermined breaking area by which the first locking member and the second locking member are rotationally fixed with respect to each other.

18. A method for using a polyaxial bone anchoring device having a bone anchoring element having a shank and a head, a receiving part having a channel and a central axis, a rod, a pressure element, a locking assembly having a first locking member having a first end, a second end and a bore passing through the first locking member from the first end to the second end and the bore having a bore axis and a second locking member having a first end, a second end and an engagement portion, the first end of the second locking member being insertable into the second end of the first locking member such that the first end of the second locking member is directed towards the first end of the first locking member when the locking members are assembled, comprising anchoring the shank of the bone anchoring element to a bone;

coupling the receiving part to the shank and pivotably receiving the head in the receiving part;

receiving the pressure element in the receiving part;

exerting pressure with the pressure element onto the head to lock the head in the receiving part;

receiving the rod in the channel of the receiving part;

rotating the second locking member relative to the first locking member in a second direction in the bore of the first locking member until the first locking member and the second locking member are rotationally fixed relative to each other such that by rotating the second locking member via the engagement portion in a first direction, the first locking member is rotated together with the second locking member in the first direction and advanced in an axial direction;

inserting the locking assembly into the channel of the receiving part so that the second end of the first locking member faces the pressure element;

advancing the locking assembly into the channel of the receiving part with the engagement portion so that the first locking member contacts the pressure element with at least a surface portion of its second end;

rotating the second locking member within the first locking member with the engagement portion in the first direction so that the second locking member contacts the rod with at least a surface portion of its second end; and wherein in a first configuration in which the locking members are assembled in the channel, the first locking member and the second locking member are rotationally fixed relative to each other such that by application of a first torque to the second locking member via the engagement portion in the first direction, the first locking member is rotatable together with the second locking member in the first direction and configured to be advanced in the axial direction to contact the pressure member with at least the surface portion of its second end and in a second configuration in which the locking members are assembled in the channel, the second locking member is rotatable within the first locking member such that by rotating the second locking member via the engagement portion in the first direction, the second locking member is configured to be advanced in the axial direction to contact the rod with at least the surface portion of its second end, wherein in the first configuration, the first end of the second locking member abuts against an abutment of the first locking member.

* * * * *